United States Patent
Hollopeter et al.

(10) Patent No.: US 10,363,114 B2
(45) Date of Patent: Jul. 30, 2019

(54) AIMING AND STATUS INDICATOR SYSTEM FOR SURGICAL LIGHTHEADS AND CAMERAS

(71) Applicant: American Sterilizer Company, Mentor, OH (US)

(72) Inventors: Michael Hollopeter, Kirtland, OH (US); Damon Jurkiewicz, Cleveland, OH (US); David Jesurun, South Euclid, OH (US); Lena Tana Fogle, Fairfield, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 15/788,032

(22) Filed: Oct. 19, 2017

(65) Prior Publication Data
US 2018/0116755 A1    May 3, 2018

Related U.S. Application Data

(60) Provisional application No. 62/415,570, filed on Nov. 1, 2016.

(51) Int. Cl.
*A61B 90/35* (2016.01)
*A61B 90/00* (2016.01)
(Continued)

(52) U.S. Cl.
CPC .............. *A61B 90/35* (2016.02); *A61B 90/30* (2016.02); *A61B 90/361* (2016.02); *F21S 8/046* (2013.01);
(Continued)

(58) Field of Classification Search
None
See application file for complete search history.

(56) References Cited

U.S. PATENT DOCUMENTS 4,634,230 A * 1/1987 Spezio ................... G01S 3/043
                                                          342/54
4,651,257 A    3/1987 Gehly
(Continued)

FOREIGN PATENT DOCUMENTS

CN    204484149 U    7/2015   ............... A61B 6/04
DE    102009009549 A1    2/2009   ............. A61B 19/00

OTHER PUBLICATIONS

Krupa et al., "Autonomous 3-D Positioning of Surgical Instruments in Robotized Laparoscopic Surgery using Visual Servoing," IEEE Transactions on Robotics and Automation, vol. 19, No. 5, Oct. 2003, pp. 842-853.
(Continued)

*Primary Examiner* — Chico A Foxx
(74) *Attorney, Agent, or Firm* — Kusner & Jaffe

(57) ABSTRACT

An aiming and status indicator system for surgical lightheads, cameras, and other lighting system accessory devices. The system includes a plurality of marker lights mounted to a housing for the accessory device. Each marker light produces a respective marker light beam that is directed towards a work area (surgical site) to provide a marker indicator pattern. The marker indicator patterns can be used to indicate the boresight of a lighthead or camera, whether a lighthead is in a focused or unfocused condition, and status information associated with the lighting system.

20 Claims, 6 Drawing Sheets

(51) Int. Cl.
  *F21V 23/04* (2006.01)
  *F21V 33/00* (2006.01)
  *F21V 21/14* (2006.01)
  *F21V 23/00* (2015.01)
  *G08B 5/36* (2006.01)
  *F21S 8/04* (2006.01)
  *A61B 90/30* (2016.01)
  *F21Y 115/10* (2016.01)
  *A61B 18/20* (2006.01)
  *F21W 131/205* (2006.01)
  *A61B 90/13* (2016.01)

(52) U.S. Cl.
  CPC ............ *F21V 33/0068* (2013.01); *G08B 5/36* (2013.01); *A61B 18/20* (2013.01); *A61B 90/13* (2016.02); *A61B 2090/0807* (2016.02); *F21V 21/14* (2013.01); *F21V 23/003* (2013.01); *F21V 23/0471* (2013.01); *F21W 2131/205* (2013.01); *F21Y 2115/10* (2016.08)

(56) References Cited

U.S. PATENT DOCUMENTS

| | | | |
|---|---|---|---|
| 5,553,115 A | 9/1996 | Odaka et al. | 378/206 |
| 5,782,842 A | 7/1998 | Kloess et al. | 606/130 |
| 6,513,962 B1 * | 2/2003 | Mayshack | F21V 3/04 |
| | | | 362/583 |
| 6,633,328 B1 | 10/2003 | Byrd et al. | |
| 6,715,904 B2 | 4/2004 | Naughton | 362/399 |
| 7,083,366 B2 | 8/2006 | Tung | 408/16 |
| 7,147,371 B2 | 12/2006 | Hecker | 378/206 |
| 8,002,795 B2 | 8/2011 | Beetel | |
| 8,295,909 B2 * | 10/2012 | Goldbach | A61B 90/36 |
| | | | 600/407 |
| 8,687,172 B2 * | 4/2014 | Faul | G01C 3/08 |
| | | | 356/3.01 |
| 9,114,494 B1 | 8/2015 | Mah | B23Q 17/2233 |
| 9,310,096 B2 | 4/2016 | Schreiber | F24F 13/078 |
| 2002/0089857 A1 | 7/2002 | Borders et al. | |
| 2002/0141460 A1 | 10/2002 | Slater | |
| 2003/0206613 A1 * | 11/2003 | Collins | A61N 5/1049 |
| | | | 378/84 |
| 2009/0102396 A1 | 4/2009 | Petrucci et al. | |
| 2012/0259178 A1 * | 10/2012 | Kim | A61B 42/10 |
| | | | 600/249 |
| 2013/0221183 A1 | 8/2013 | Volkenand et al. | 248/550 |
| 2014/0267658 A1 | 9/2014 | Speier et al. | |
| 2015/0156461 A1 * | 6/2015 | Jessop | H04N 7/18 |
| | | | 348/47 |
| 2015/0182293 A1 * | 7/2015 | Yang | A61B 5/064 |
| | | | 600/424 |
| 2015/0300816 A1 * | 10/2015 | Yang | A61B 90/35 |
| | | | 600/424 |
| 2016/0091170 A1 | 3/2016 | Watanabe et al. | F21V 7/04 |
| 2016/0093063 A1 | 3/2016 | Gonzalez | |
| 2017/0030573 A1 | 2/2017 | Alexanderson et al. | F21V 33/0068 |
| 2017/0245946 A1 * | 8/2017 | Tabandeh | A61B 90/37 |
| 2017/0265943 A1 * | 9/2017 | Sela | G06F 19/00 |
| 2017/0340394 A1 * | 11/2017 | Gemmel | A61B 34/20 |

OTHER PUBLICATIONS

Hill-Rom, Trumpf Medical, TruLight 5000 Product Brochure, Sep. 30, 2015, pp. 1-8.
STERIS Harmony® vLED Surgical Lighting System Product Brochure, Oct. 2012, pp. 1-8.
STERIS Surgical Solutions, HarmonyAIR® Equipment Columns and Supply Heads Product Brochure, Oct. 2016, pp. 1-8.

* cited by examiner

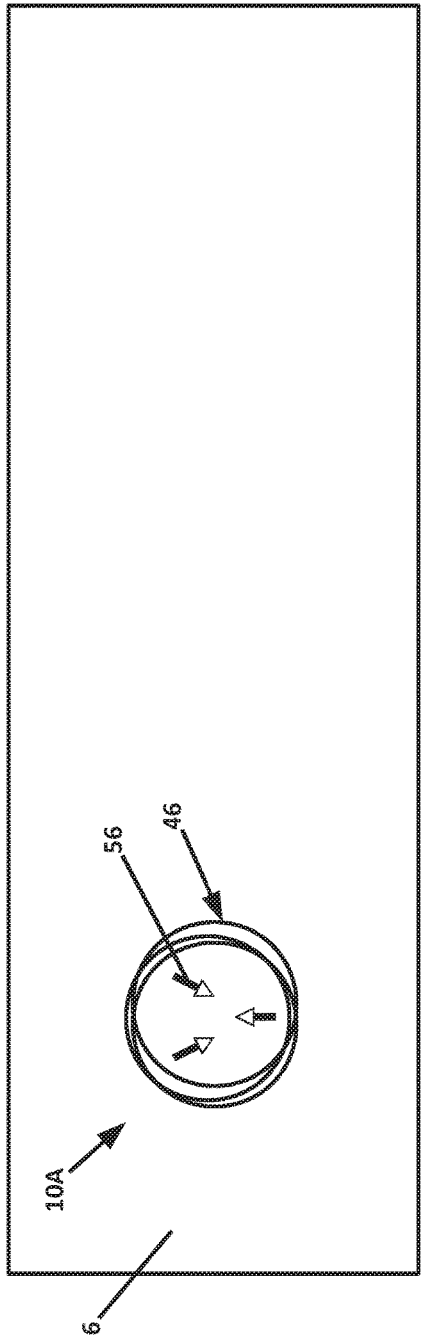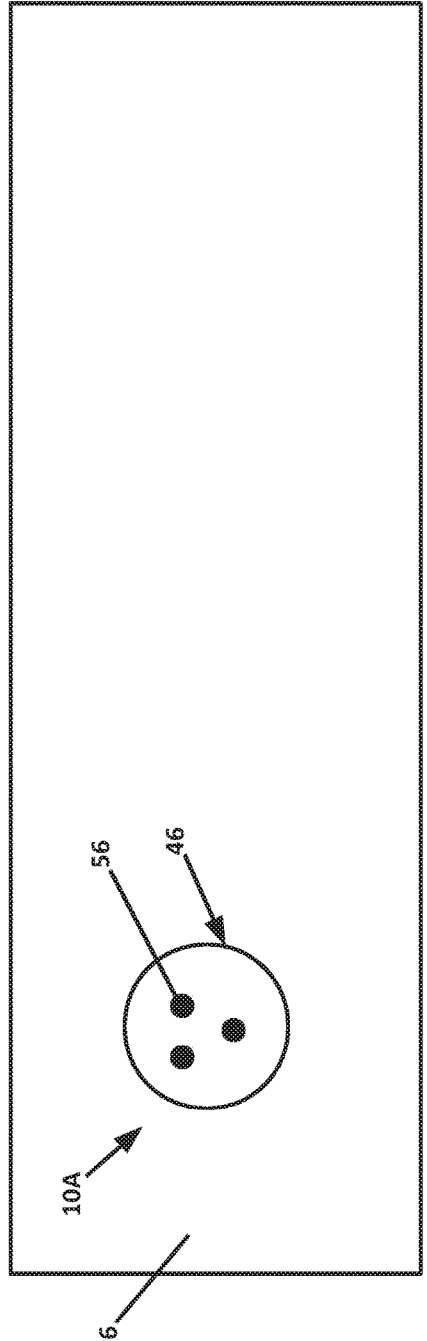

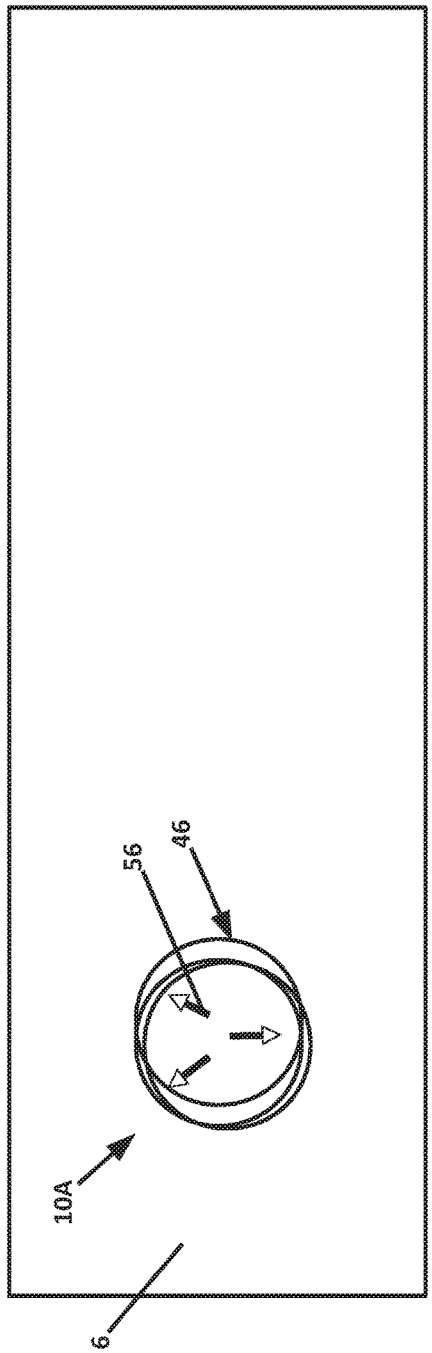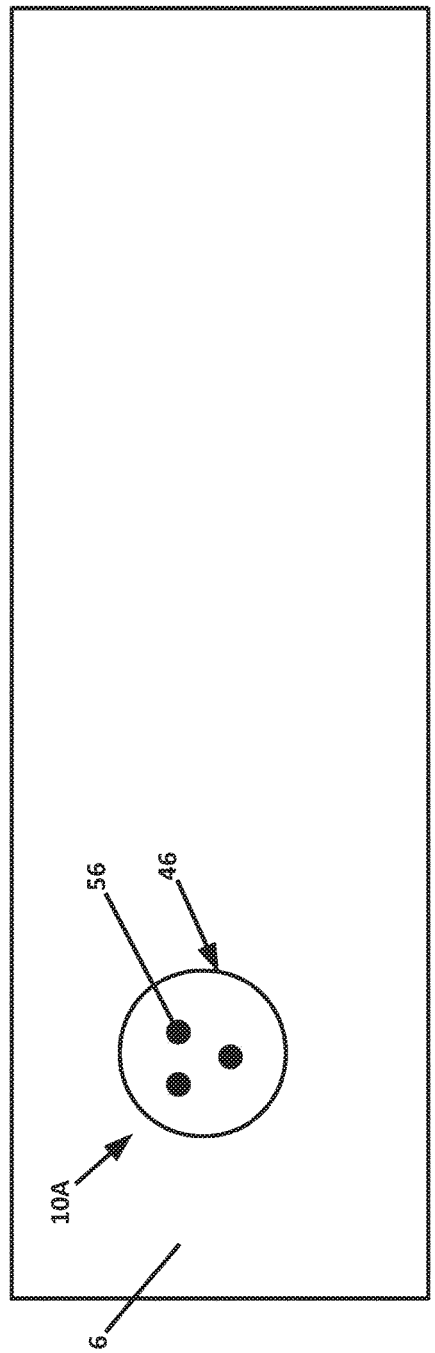

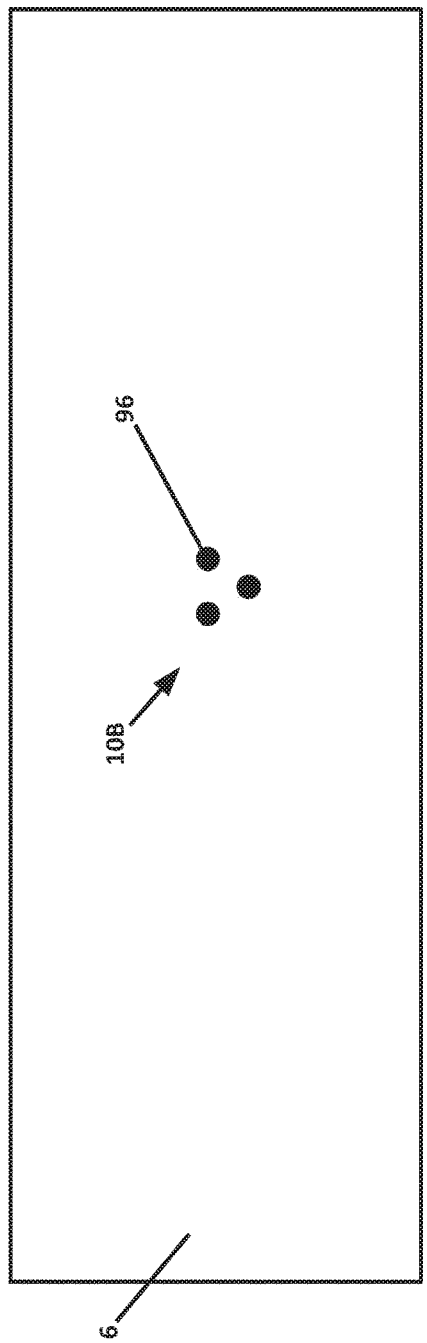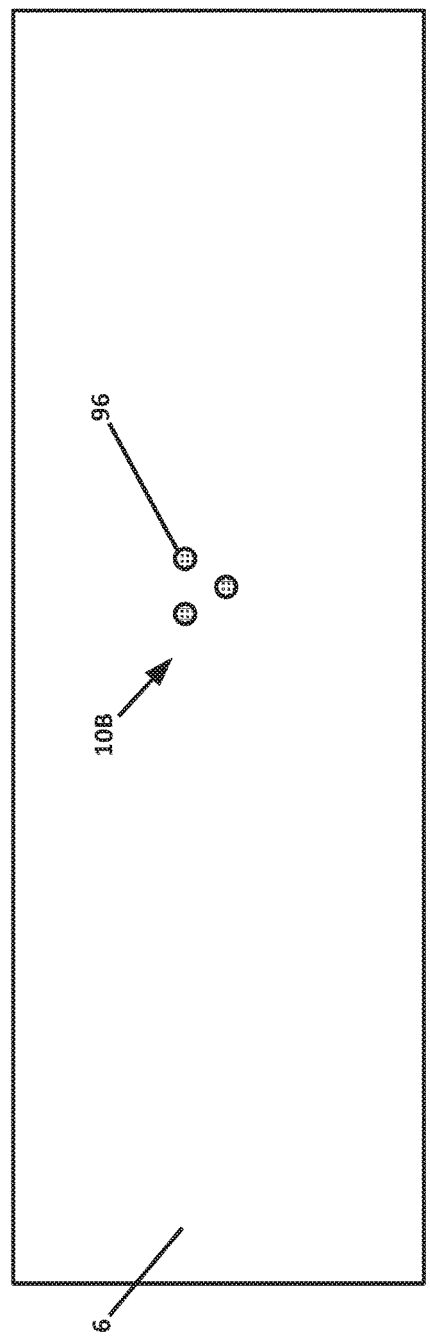

AIMING AND STATUS INDICATOR SYSTEM FOR SURGICAL LIGHTHEADS AND CAMERAS

RELATED APPLICATIONS

This application claims the benefit of U.S. Provisional Application No. 62/415,570, filed Nov. 1, 2016, and is hereby fully incorporated herein by reference.

FIELD OF THE INVENTION

The present invention relates generally to an indicator system for use with a surgical lighting system, and more particularly to an aiming and status indicator system for surgical lightheads and cameras.

BACKGROUND OF THE INVENTION

Surgical lighting systems are used in operating rooms to illuminate a work area (e.g., a surgical site). The surgical lighting systems include one or more lightheads that are typically mounted to a movable support structure. Each lighthead includes a plurality of individual light sources (e.g., LED lighting modules or LED lighting pods), wherein each light source provides a respective light beam. To achieve optimum lighting conditions at the work area, the lighthead must be properly aimed and focused.

A lighthead is aimed by physical moving the lighthead to point the light beams at the work area. The light beams produce a circular light beam pattern (e.g., a 6-12 inch diameter pattern), with the greatest illuminance coming from the center of the light beam pattern. The "boresight" of the lighthead corresponds with the center of the light beam pattern. The illumination of deep cavities at the work area may suffer due to non-optimum aiming of the lighthead, or the center of the light beam pattern may be directed at sterile drapes surrounding a surgical incision rather than the incision itself, thereby resulting in eye fatigue. In existing surgical lighting systems there is no mechanism for precisely indicating to a user (e.g., a surgeon or other medical personnel) where the center of the light beam pattern is pointing, especially when multiple lightheads are being used to illuminate the same work area. With existing surgical lighting systems, users have determined where the center of light beam pattern is pointing by physically relocating the lighthead so that the center of the light beam pattern can be observed away from the work area.

With regard to lighthead focus, the light beams provided by each light source of the lighthead may be focused to converge at a common intersection point (i.e., the focal point) to produce the circular light pattern at the work area, with the greatest illuminance at the center of the light pattern. When all of the light beams of the lighthead are properly focused (i.e., adjusted to the optimum focus distance), the lighthead provides (i) a uniform circular light pattern, (ii) maximized illuminance, and (iii) minimized shadow effects caused by any blockage of a light beam. Existing lighting systems provide adjustable lighthead focus by use of solid state lighting control or by mechanical movement of the lighthead or light sources of the lighthead. However, these lighting systems do not have a mechanism that clearly indicates to the user that the lighthead is set to the optimum focus distance, thereby resulting in sub-optimal lighting conditions at the work area.

Furthermore, lighting systems for illuminating surgical sites are typically capable of a light output as high as 160,000 lux. This level of light output results in high intensity reflection that makes it difficult to determine whether a lighthead is properly aimed and/or optimally focused.

A surgical camera (e.g., a lighthead-mounted camera or a standalone suspension-mounted camera) is typically aimed by a user over a surgical site by watching the image produced by the camera on a monitor located away from the surgical site. This method of aiming the camera is not ideal, since the image has no true reference or orientation, and requires time for the user to adapt to inversion of the image from the positioning reference.

The present invention addresses these and other drawbacks of the prior art by providing an aiming and status indicator system for surgical lightheads and cameras.

SUMMARY OF THE INVENTION

In accordance with the present invention, there is provided a lighting system comprising of a support assembly; a control unit for controlling operation of the lighting system; and a lighting system accessory device mounted to the support assembly, the lighting system accessory device having a plurality of marker lights mounted thereto, each marker light providing a respective marker indicator pattern, wherein the marker indicator patterns have a geometric center that corresponds to a boresight of the accessory device.

In accordance with another aspect of the present invention, there is provided a lighting system comprising of a support assembly; a control unit for controlling operating of the lighting system; and a lighthead mounted to the support assembly, the lighting system accessory device having a plurality of marker lights mounted thereto, each marker light providing a respective marker indicator pattern, wherein the marker indicator patterns have a geometric center that corresponds to a boresight of the lighthead.

An advantage of the present invention is the provision of an aiming and status indicator system that provides a user with a visual indicator for accurately aiming the center of a lighthead light beam pattern at a work area.

Another advantage of the present invention is the provision of an aiming and status indicator system that provides a user with immediate visual feedback concerning the status of lighthead focus.

Still another advantage of the present invention is the provision of an aiming and status indicator system that does not require surgical staff to look away from a work area in order to determine lighthead aiming or focus status.

Still another advantage of the present invention is the provision of an aiming and status indicator system that does not require a user to physically move a lighthead light beam away from a work area in order to determine the center of a lighthead light beam pattern.

Still another advantage of the present invention is the provision of an aiming and status indicator system that has different operating states indicative of system operating conditions, surgeon-related and patient-related events, and operating room conditions.

Yet another advantage of the present invention is the provision of an aiming and status indicator system that provides a user with a visual indicator for accurately aiming the center of a surgical camera at a work area without viewing a monitor.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein:

FIG. 4A shows marker indicator patterns in a first state indicative of a lighthead in an unfocused condition, where the distance between the lighthead and the work area needs to be decreased to optimally focus the lighthead;

FIG. 4B shows marker indicator patterns in a second state indicative of a lighthead in a focused condition;

FIG. 5A shows marker indicator patterns in a first state indicative of a lighthead in an unfocused condition, where the distance between the lighthead and the work area needs to be increased to optimally focus the lighthead;

FIG. 5B shows marker indicator patterns in a second state indicative of a lighthead in a focused condition;

FIG. 6A shows marker indicator patterns in a first state indicative of a normal operating condition for the lighting system; and FIG. 6B shows marker indicator patterns in a second state indicative of a fault condition for the lighting system.

DETAILED DESCRIPTION OF THE INVENTION

Figure 1:
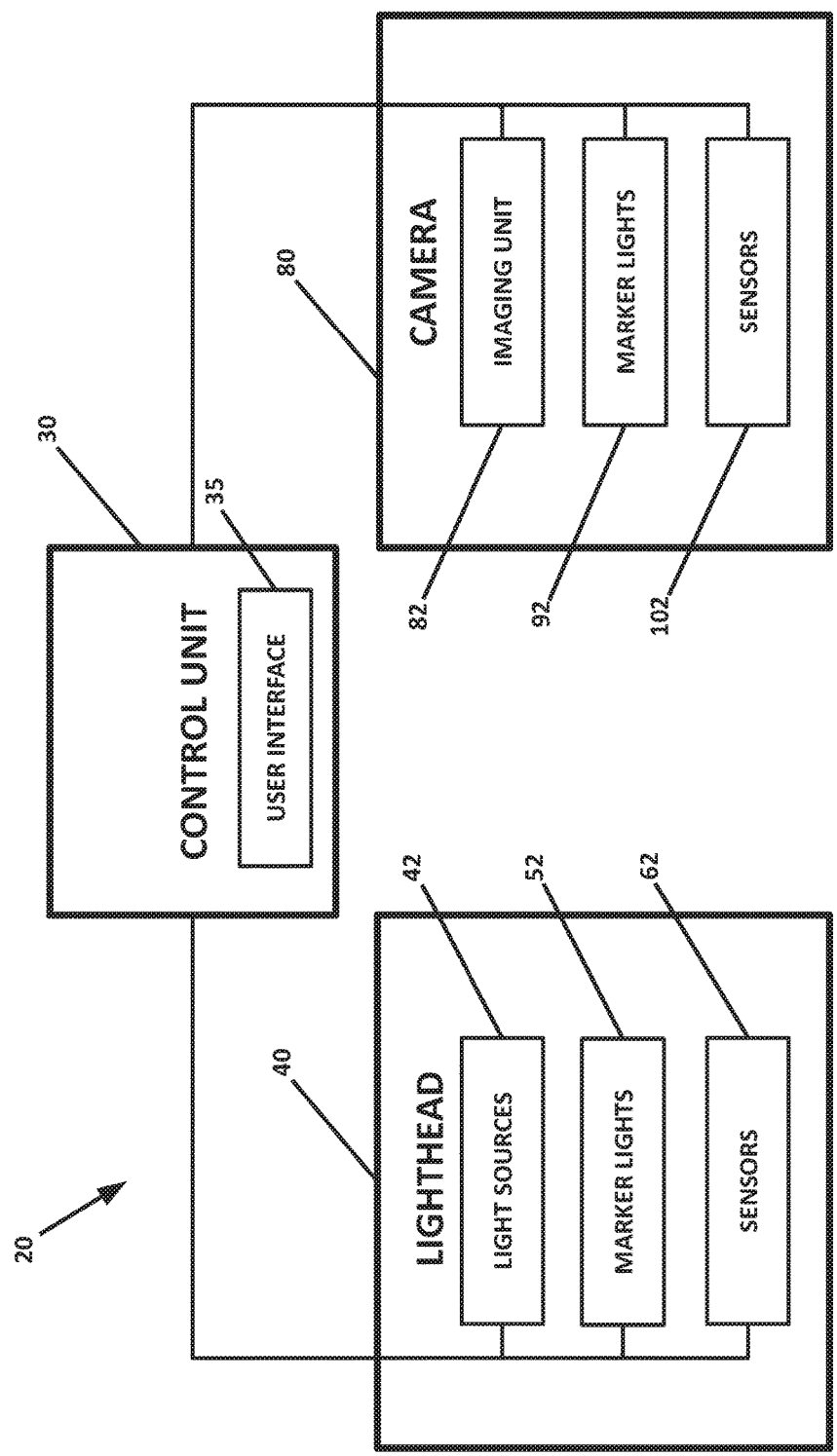
FIG. 1 is a block diagram of a lighting system that includes an aiming and status indicator system according to an embodiment of the present invention.
Figure 2:
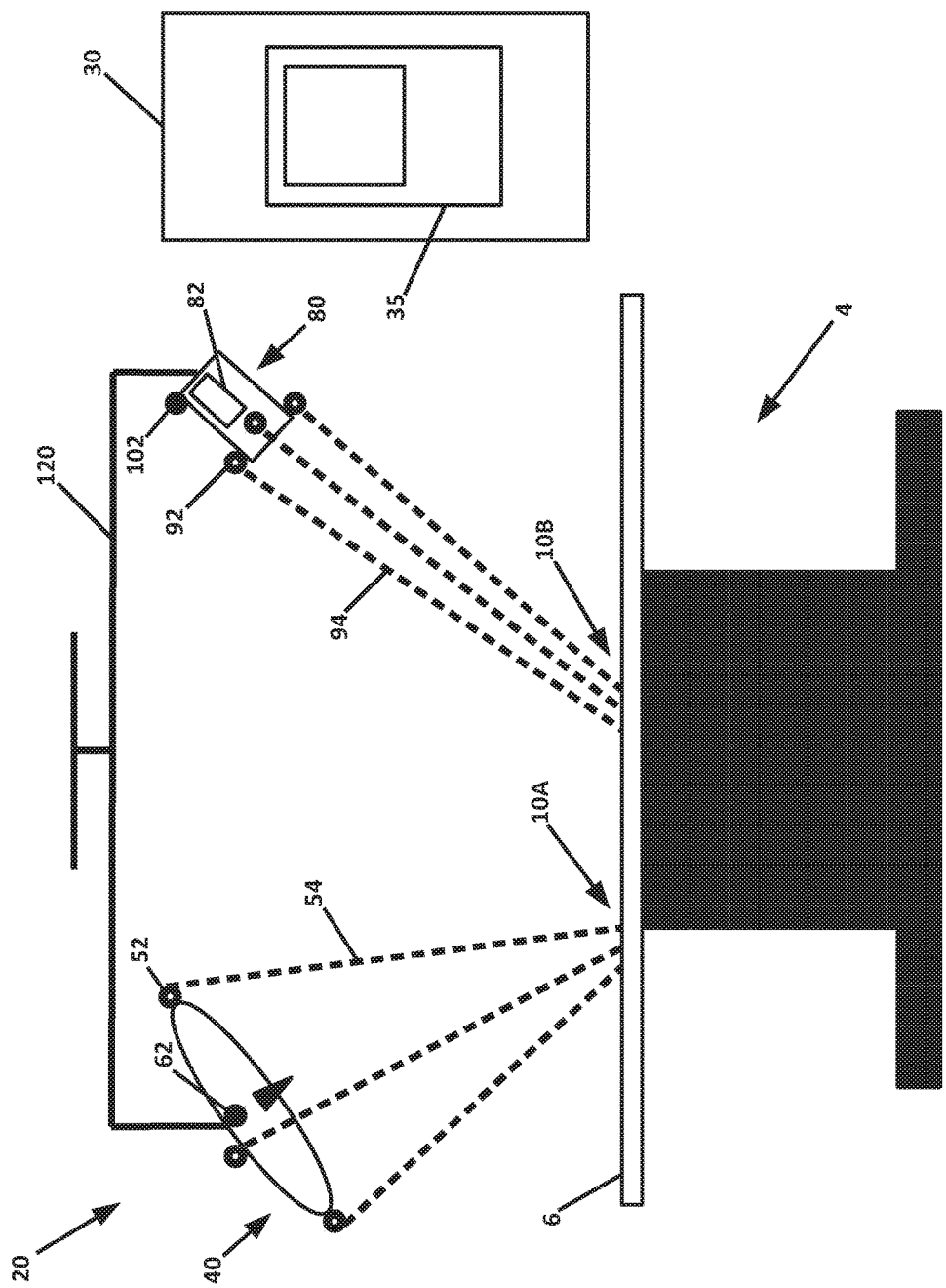
FIG. 2 is a schematic illustration of the lighting system shown in FIG. 1.

Referring now to the drawings wherein the showings are for the purposes of illustrating an embodiment of the invention only and not for the purposes of limiting same, FIG. 1 shows an example lighting system 20 that includes an aiming and status indicator system according to an embodiment of the present invention. FIG. 2 provides a schematic illustration of lighting system 20. In the illustrated embodiment, lighting system 20 is generally comprised of a control unit 30 having an associated user interface 35, and one or more accessory devices. In the example lighting system 20, the accessory devices take the form of a lighthead 40 and a camera 80. Lighting system 20 also includes a support assembly for supporting the accessory devices above a surgical table 4 having a work surface 6. The support assembly may take the form of a conventional suspension system 120, as schematically shown in FIG. 2. As known to those skilled in the art, suspension system 120 is generally comprised of a plurality of suspension arms, hubs, mounts, yokes, and the like. Suspension system 120 is configured to allow repositioning of accessory devices relative to work surface 6 of surgical table 4.

The example configuration of lighting system 20 of FIGS. 1 and 2 is shown solely for illustrating an embodiment of the present invention. In this regard, it should be appreciated that the present invention is intended for use with alternative configurations of lighting system 20. In this respect, lighting system 20 may include various combinations of accessory devices, including, but not limited to, lightheads, cameras, video cameras, video monitors, surgical lasers, and the like.

Control unit 30 is a conventional microprocessor-based computer system that is in communication with the accessory devices, (i.e., lighthead 40 and camera 80). User interface 35 may take the form of an interface device, including, but not limited to, a touchscreen, a control panel, a keypad, a remote control, a wall-mount control, and the like. User interface 35 may be a wired or wireless device.

In the illustrated embodiment, lighthead 40 is generally comprised of a plurality of light sources 42, marker lights 52, and sensors 62. Each light source 42 may take the form of an LED lighting module or an LED lighting pod. A respective light beam is produced by each light source 42.

Marker lights 52 are components of the aiming and status indicator system of the present invention. Marker lights 52 may take the form of a colored laser light source that is mounted to or within a housing for lighthead 40. It is contemplated that marker lights 52 may alternatively take the form of colored LEDs, or other lighting devices. In the illustrated embodiment, marker lights 52 are mounted to the periphery of the housing for lighthead 40, as schematically shown in FIG. 2. As will be described in further detail below, each marker light 52 provides a marker beam 54 that produces a marker indicator pattern 56 that may be seen on work surface 6, as shown in FIGS. 3A and 3B, FIGS. 4A and 4B, and FIGS. 5A and 5B. It is contemplated that marker indicator pattern 56 may take a variety of shapes, including, but not limited to, a dot, a crosshair, an arrowhead, a chevron, a non-symmetric design element, and the like.

The marker indicator patterns 56 of marker lights 52 provide a boresight indicator for aiming lighthead 40. In this regard, marker lights 52 are symmetrically spaced such that the geometric center of marker indicator patterns 56 is the center of light beam pattern 46 produced by light sources 42. In the illustrated embodiment, there are three (3) marker lights 52. However, it is contemplated that there may be more than three (3) marker lights 52. Marker lights 52 may also have a plurality of operating states, wherein each state of marker lights 52 provides a marker indicator pattern 56 with a different visual indicator. For example, the different visual indicators may include, but are not limited to, different colors, different shapes, different light intensities (e.g., dim/bright), light OFF, static light ON, flashing light, pulsing light, blinking light, and the like. The different operating states can be used to indicate various operating conditions (i.e., system status) to the user, including, but not limited to, non-optimum focus distance (too far or too close), optimum focus distance, indication of light beam intensity, color temperature, normal operating conditions, fault conditions (such as operating on battery backup), system warnings, and system failures. The different operating states could also be used to indicate surgeon-related events, patient-related events, and operating room conditions (e.g., patient monitoring status, incoming phone calls, and timekeeping). The patient monitoring status may include patient temperature indication (e.g., entering hypothermia), patient interface pressure accumulation, or patient vitals.

Sensors 62 include, but are not limited to, distance sensors, accelerometers, encoders, and the like. Sensors 62 may be mounted to the housing for light sources 42 of lighthead 40. Control unit 30 receives signals from sensors 62 that can be used to determine whether lighthead 40 has been moved to reposition light sources 42, and whether light sources 42 are located at the optimum focus distance relative to work surface 6.

In accordance with an embodiment of the present invention, control unit 30 may be programmed to temporarily activate marker lights 52 when sensors 62 (e.g., a distance sensor and an accelerometer) transmit signals indicating that lighthead 40 has been physically moved or the distance between light sources 42 and work surface 6 has been changed (e.g., surgical table 4 is raised or lowered relative to light surgical light 40). Marker lights 52 may also be temporarily activated when the focus of light sources 42 has been manually or electronically adjusted by operation of user interface 35 (e.g., by use of optics (lens) or by a mechanical repositioning (tilt) of the light sources within the lighthead).

After a predetermined period of time, marker lights 52 may be deactivated (e.g., turned OFF). The automated activation of marker lights 52 eliminates the need for the user to touch sterile parts of lighthead 40 in order to activate marker lights 52. User interface 35 may also display a control parameter that allows the user to manually activate/deactivate marker lights 52.

In the illustrated embodiment, camera 80 is generally comprised of an imaging unit 82, marker lights 92, and sensors 102. Imaging unit 82 may take the form of a conventional digital image sensor, such as a CCD or CMOS sensor.

Marker lights 92 are components of the aiming and status indicator system of the present invention. Marker lights 92 are substantially the same as marker lights 52 described above. In the illustrated embodiment, marker lights 92 take the form of a colored laser light source that is mounted to or within a housing for camera 80. More specifically, marker lights 92 are mounted to the periphery of the housing for camera 80, as schematically shown in FIG. 2. Each marker light 92 produces a marker beam 94 that provides a marker indicator pattern 96 that may be seen on work surface 6, as shown in FIGS. 6A and 6B. Marker indicator patterns 96 are substantially the same as marker indicator patterns 56.

Marker indicator patterns 96 of marker lights 92 provide a boresight indicator for imaging unit 82 to facilitate aiming of camera 80. In this regard, marker lights 92 are symmetrically spaced such that the geometric center of the marker indicator patterns 96 is the center of the field of view for imaging unit 82 of camera 80. In the illustrated embodiment, there are three (3) marker lights 92. However, it is contemplated that there may be more than three (3) marker lights 92. Like marker lights 52, marker lights 92 may have a plurality of operating states, wherein each state of marker lights 92 provides a marker indicator pattern 96 with a different visual indicator.

Sensors 102 include, but are not limited to, distance sensors, accelerometers, encoders, and the like. Sensors 102 may be mounted to the housing for camera 80. Control unit 30 receives signals from sensors 102 that can be used to determine whether camera 80 has been moved to reposition camera 80 relative to work surface 6.

In accordance with an embodiment of the present invention, control unit 30 may be programmed to temporarily activate marker lights 92 when sensors 102 transmit signals indicating that camera 80 has been physically moved or the distance between imaging unit 82 and work surface 6 has been changed. After a predetermined period of time, marker lights 92 are deactivated (e.g., turned OFF). The automated activation of marker lights 92 eliminates the need for the user to touch sterile parts of camera 80 in order to activate marker lights 92. User interface 35 may also display a control parameter that allows the user to manually activate/deactivate marker lights 92.

Figure 3A:
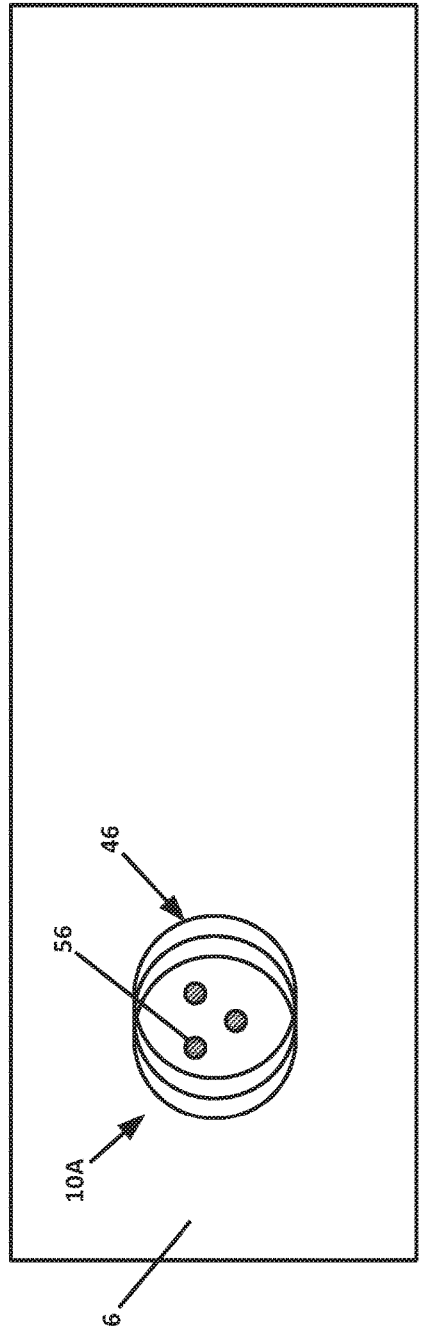
FIG. 3A shows marker indicator patterns in a first state indicative of a lighthead in an unfocused condition.
Figure 3B:
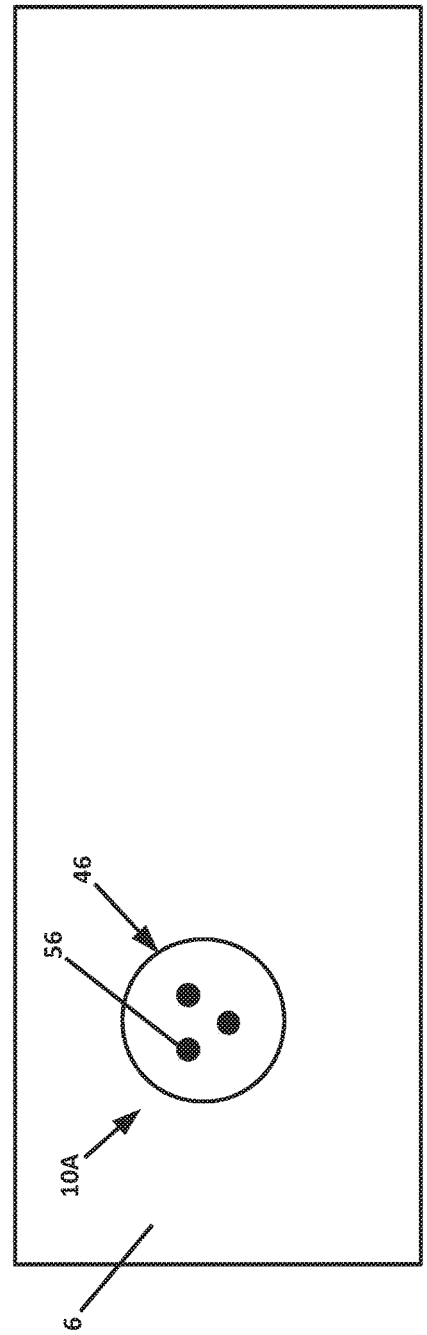
FIG. 3B shows marker indicator patterns in a second state indicative of a lighthead in a focused condition.

FIG. 3A shows a work area 10A on work surface 6. In this figure, lighthead 40 is in an unfocused condition, as can be observed from the unfocused light beam pattern 46 (i.e., non-converging light beams). Accordingly, marker lights 52 are in a first state that provides marker beam patterns 56 comprising dots in a first color (e.g., red). When lighthead 40 is in the optimal focused condition, marker lights 52 change to a second state that provides marker beam patterns 56 comprising the dots in a second color (e.g., green), as shown in FIG. 3B.

FIG. 4A also shows a work area 10A on work surface 6. In this figure, lighthead 40 is in an unfocused condition that requires the distance to be reduced between light sources 42 and work surface 6. Accordingly, marker lights 52 are in a first state that provides marker beam patterns 56 comprising inward pointing arrows in a first color. When lighthead 40 is in the optimal focused condition, marker lights 52 change to a second state that provides marker beam patterns 56 comprising dots in a second color, as shown in FIG. 4B.

FIGS. 5A and 5B are similar to FIGS. 4A and 4B. However, in FIG. 5A the marker lights 52 are in a first state that provides marker beam patterns 56 comprising outward pointing arrows in a first color. This indicates to a user that focusing of lighthead 40 requires the distance to be increased between light sources 42 and work surface 6. When lighthead 40 is in the optimal focused condition, marker lights 52 change to a second state that provides marker beam patterns 56 comprising dots in a second color, as shown in FIG. 5B.

FIG. 6A shows marker indicator patterns 96 provided by marker lights 92 associated with camera 80. As indicated above, the geometric center of the marker indicator patterns is used to aim imaging unit 82 at work area 10B. In the illustrated embodiment, marker lights 92 are in a first state that provides marker beam patterns 96 comprising dots in a first color. In this embodiment, the dots in a first color are indicative of lighting system 20 operating under normal operating condition. In contrast, marker lights 92 shown in FIG. 6B are changed to a second state that provide marker beam patterns 96 comprising dots in a second color. In this embodiment, the dots in a second color are indicative of lighting system 20 operating under a fault condition.

The foregoing describes specific embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A lighting system, comprising:
   a support assembly;
   a control unit for controlling operation of the lighting system; and
   an accessory device mounted to the support assembly, the accessory device having an aiming and status indicator system comprising a plurality of marker lights mounted to the accessory device, each marker light providing a respective marker indicator beam aimed onto a work area to provide a respective marker indicator pattern on the work area, wherein the marker indicator patterns simultaneously indicate: (i) a geometric center that corresponds to a boresight of the accessory device for aiming the accessory device; and (ii) an operating condition.

2. The lighting system of claim 1, wherein the marker indicator patterns have different visual indicators for indicating different operating conditions.

3. The lighting system of claim 2, wherein the visual indicators are selected from the group including: different colors, different shapes, different light intensities, light OFF, static light ON, flashing light, pulsing light, and blinking light.

4. The lighting system of claim 1, wherein said operating condition is selected from the group including: non-optimum focus distance, optimum focus distance, indication of light beam intensity, color temperature, normal condition, fault condition, system warnings, lighting system failures, surgeon related events; patient related events, and operating room conditions.

5. The lighting system of claim 1, wherein the accessory device includes a sensor that generates a signal when movement of the accessory device is sensed, said marker lights activated in response to the sensed movement of the accessory device.

6. The lighting system of claim 1, wherein the accessory device includes a sensor that generates a signal when a distance between the accessory device and a work surface is sensed, said marker lights activated in response to the sensed change to the distance.

7. The lighting system of claim 1, wherein the marker lights are laser lights.

8. The lighting system of claim 1, wherein the marker indicator pattern has a shape that is selected from one of the following shapes: a dot, an arrow, a crosshair, an arrowhead, a chevron, and a non-symmetric design element.

9. The lighting system of claim 1; wherein the accessory device is a surgical lighthead comprised of a plurality of light sources that produce light beam patterns.

10. The lighting system of claim 1, wherein the accessory device is a surgical camera comprised of an imaging unit.

11. The lighting system of claim 1, wherein the accessory device is a video camera.

12. The lighting system of claim 1, wherein the accessory device is a surgical laser.

13. A lighting system, comprising:
a support assembly;
a control unit for controlling operation of the lighting system; and
a lighthead mounted to the support assembly, the lighthead including an aiming and status indicator system having a plurality of marker lights mounted to the lighthead, each marker light providing a respective marker indicator pattern on a work area, wherein the marker indicator patterns simultaneously indicate: (i) a geometric center that corresponds to a boresight of the lighthead for aiming the lighthead; and (ii) an operating condition.

14. The lighting system of claim 13, wherein the marker lights are mounted to a housing for the lighthead.

15. The lighting system of claim 13, wherein the marker indicator patterns have different visual indicators for indicating different operating conditions.

16. The lighting system of claim 15, wherein the visual indicators are selected from the group including: different colors, different shapes, different light intensities, light OFF, static light ON, flashing light, pulsing light, and blinking light.

17. The lighting system of claim 13, wherein said operating condition is non-optimum focus distance for the lighthead or optimum focus distance for the lighthead.

18. The lighting system of claim 13, wherein said operating condition is a normal condition for the lighting system or a fault condition for the lighting system.

19. The lighting system of claim 13, wherein the lighthead includes a sensor that generates a signal when movement of the lighthead is sensed, said marker lights activated in response to the sensed movement of the lighthead.

20. The lighting system of claim 13, wherein the lighthead includes a sensor that generates a signal when a distance between the lighthead and a work surface is sensed, said marker lights activated in response to the sensed change to the distance.

* * * * *